United States Patent
Sun

(10) Patent No.: US 6,334,222 B1
(45) Date of Patent: Jan. 1, 2002

(54) SOCK FOR ATHLETE'S FOOT

(75) Inventor: Sanxing Sun, 38 Padanaram Ave., B21, Danbury, CT (US) 06811

(73) Assignee: Sanxing Sun

( * ) Notice: Subject to any disclaimer, the term of this patent is extended or adjusted under 35 U.S.C. 154(b) by 0 days.

(21) Appl. No.: 09/635,580

(22) Filed: Aug. 9, 2000

(51) Int. Cl.[7] .................................................. A41B 11/00
(52) U.S. Cl. ................................................ 2/239; 2/409
(58) Field of Search ........................................ 2/239, 409

(56) References Cited

U.S. PATENT DOCUMENTS

| | | | | |
|---|---|---|---|---|
| 1,452,302 A | * | 4/1923 | Loven | 2/239 |
| 1,798,201 A | * | 3/1931 | Hedges | 2/239 |
| 2,932,829 A | * | 4/1960 | Corbin | 2/239 |
| D189,206 S | * | 11/1960 | Thompson | 2/239 |
| 3,023,420 A | * | 3/1962 | Tann | 2/239 |
| 3,128,763 A | * | 4/1964 | Langenfeld et al. | 2/239 |
| 4,261,061 A | * | 4/1981 | McAlvage | 2/239 |
| 5,054,129 A | * | 10/1991 | Baehr | 2/409 |
| 5,623,734 A | * | 4/1997 | Pugliatti | 2/239 |
| 5,774,898 A | * | 7/1998 | Malpee | 2/239 |
| 5,867,838 A | * | 2/1999 | Corry | 2/239 |
| 5,906,007 A | * | 5/1999 | Roberts | 2/239 |

* cited by examiner

*Primary Examiner*—Gloria M. Hale

(57) ABSTRACT

A sock for preventing athlete's foot includes sheaths at the toe portion of the foot that can reach, cover, and fit into areas between toes. The sheaths can absorb moist, greasy and other secretions between toes and keep skins in the area dry. This prevents microscopic fungi from thriving between toes. The sheath portion remains integral with the rest of the sock that may also include a foot body, heel, ankle, and leg engaging portion.

3 Claims, 3 Drawing Sheets

SOCK FOR ATHLETE'S FOOT

BACKGROUND OF THE INVENTION

The present invention relates to socks, and more particular to socks that include sheaths at the toe portion to reach, cover and fit into areas between toes in order to absorb the moist and greasy secretions. This keeps the skin in the area dry and therefore prevents microscopic fungi thriving between toes.

Athlete's foot is an infectious skin disease caused by a type of microscopic fungus that involves itching, scaling, inflammation, and blisters on the foot, usually between toes. When blisters break, small raw areas of tissue are exposed, causing pain and swelling. Athlete's foot may spread to the sole and to toenails of the foot. In severe cases bacteria may thrive as a secondary infection in athlete's foot, which worsens the symptoms of the disorder and makes it more difficult to cure. The fungi thrive on warm and moist skin surfaces. As a result, the disease affects many people whose feet regularly become hot and sweaty, particularly in areas between toes because sweats and other secretions of foot skin accumulate between toes, and regular socks cannot reach and absorb the moisture in the area.

In order to prevent such phenomenon it is necessary to prevent any accumulation of moisture between toes and keep the skin in the area dry so as to prevent microscopic fingi thriving.

BRIEF SUMMARY OF THE INVENTION

The present invention is carried out for the sake of overcoming the disadvantage of regular socks that cannot reach and absorb the moisture between toes. It is particularly suitable for, but is not limited to, use by people with athlete's foot.

The sock according to the present invention includes an essential toe portion of two to five sheaths to reach, cover and fit into areas between toes. The sheath portion is integral with the rest of the sock. The feature and advantage of the present invention will be understood clearly from the following description in conjunction with the accompanying drawings.

In one embodiment the sock has a close-ended sheath for every toe of the foot that can absorb the moist, greasy and other secretions existing between toes. This keeps the skin in the area dry and therefore prevents microscopic fungi thriving between toes. Antifungal medicaments can be applied on the sheath for the same medical purpose.

In another embodiment the sock has an open-ended sheath for every toe of the foot that can absorb the moist, greasy and other secretions existing between toes. This keeps the skin in the area dry and therefore prevents microscopic fungi thriving between toes. The open-ended sheaths allow toes with different lengths to fit well into the sheath and sock. Antifungal medicaments can be applied on the sheath for the same medical purpose.

In yet another embodiment the sock includes an inner layer of five sheaths at the toe portion. The inner layer can absorb the moist, greasy and other secretions existing between toes. This keeps the skin in the area dry and therefore prevents microscopic fungi thriving between toes. The inner sheaths allow the sock look the same as a regular sock when it is worn. Antifungal medicaments can be applied on the inner sheath for the same medical purpose.

DETAILED DESCRIPTION OF THE EMBODIMENT

Figure 1:
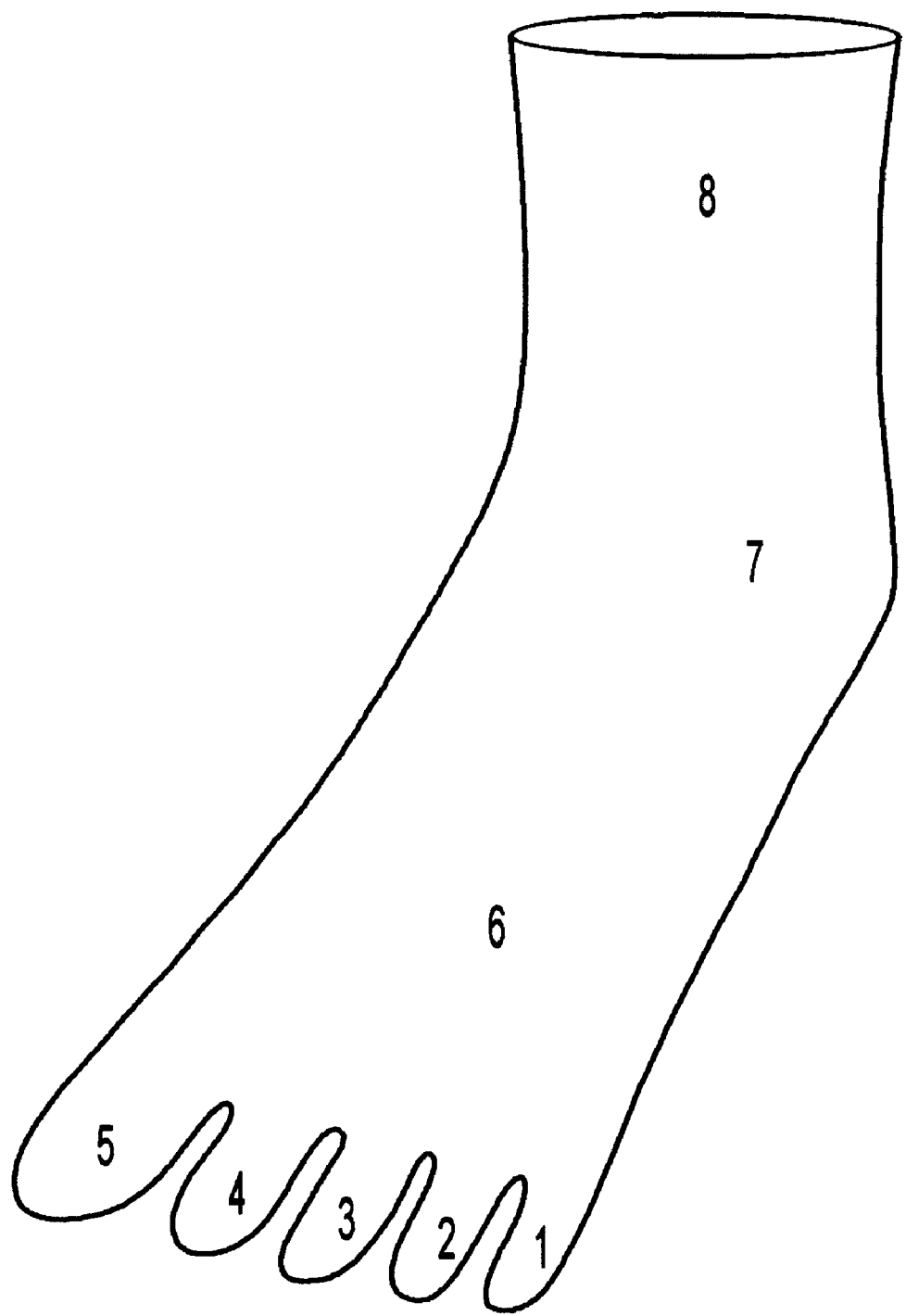
FIG. 1 is a perspective view of a sock including five sheaths. In this design the sheaths are independent to each other. Every toe has its own sheath when the sock is worn. Any sweat and secretion in areas between two adjacent toes is absorbed by the sheath.

Exemplary embodiments of the sock for preventing athlete's foot according to the present invention will now be described in detail with reference to the illustrated drawings. In FIG. 1 the sock for athlete's foot includes five sheaths numbered from 1 to 5, a foot body portion 6 that encircles the foot body, a heel portion 7, and an ankle portion 8. In this embodiment every sheath is independently knitted and it can be seen clearly there are five sheaths when the sock is worn. These sheaths permit the wearer's toes to fit in each of them and allow the sock fabric to cover and fit into areas between every two adjacent toes, and thus are able to constantly absorb secretions from areas between toes. This keeps the skin in the area dry and therefore prevents microscopic fungi thriving. The five sheaths are of different size and shape in accordance with the size and shape of toes. Thus, sheath 5 is for the big toe, sheath 2 to 4 are for the three middle toes, and sheath 1 is for the little toe. Sheaths 1 to 5 are build along the root line of toes so as to correspond to the position of five toes. The sock may be woven or knitted from many types of materials, such as natural materials cotton, wool and silk, or various types of manufactured fibers, including nylon, acrylic, polyester, polypropylene, and spandex, etc. The whole sock may be made of the same material, or alternatively, the sheath portion may be preferably made of somewhat high adsorbing material such as cotton so as to maximize its moisture adsorbing function, while other portions are made of a different material. Antifungal medications can be applied and/or permeated on the sheaths for the same medical purpose.

Figure 2:
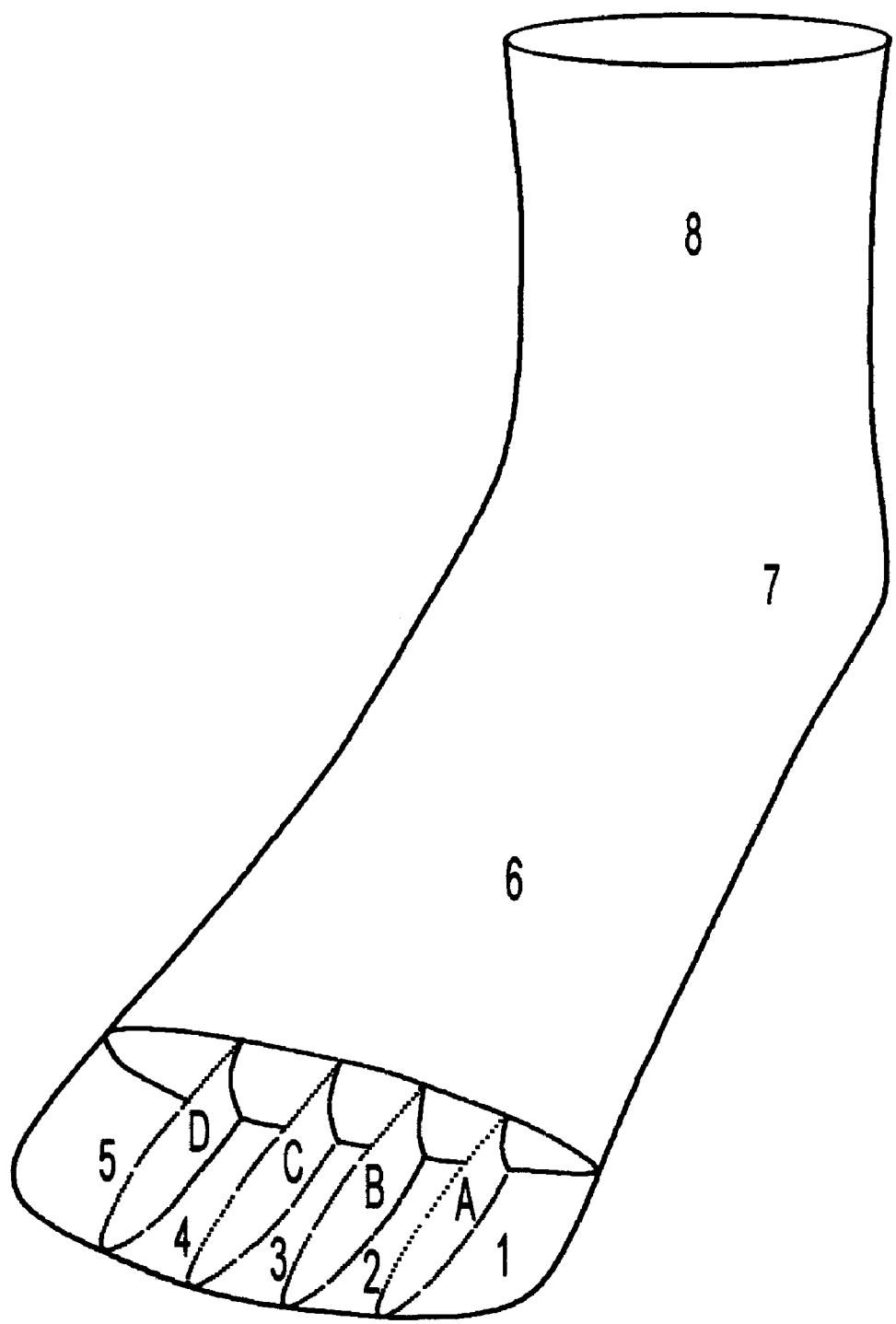
FIG. 2 is a perspective view of a sock including five sheaths. In this design there are four dividers forming five sheaths in the toe portion inside the sock. The dividers are integral with the rest of the sock. Every toe has its own sheath when the sock is worn. Any sweat and secretion between two adjacent toes is absorbed by the sheath.

In FIG. 2 the sock for athlete's foot includes five sheaths numbered from 1 to 5, a foot body portion 6 that encircles the foot body, a heel portion 7, and an ankle portion 8. In this embodiment the five sheaths are formed from four dividers A, B, C and D that are positioned between toes when the sock is worn. The four dividers are knitted, woven or sewed to both the bottom and top part of the sock at the toe portion. The four dividers and five sheaths may not be seen when the sock is worn because they are "hidden" inside the sock. These sheaths permit the wearer's toes to fit in each of them and allow the sock fabric to cover and fit into areas between every two adjacent toes, and thus are able to constantly absorb secretions from areas between toes. This keeps the skin in the area dry and therefore prevents microscopic fungi thriving. The five sheaths are of different size in accordance with the size of toes. Thus, sheath 5 is for the big toe, sheath 2 to 4 are for the three middle toes, and sheath 1 is for the little toe. Dividers A to D are build along the root line of toes so as to correspond to the position of five toes. The sock may be woven or knitted from many types of materials, such as natural materials cotton, wool and silk, or various types of manufactured fibers, including nylon, acrylic, polyester, polypropylene, and spandex, etc. The whole sock may be made of the same material, or alternatively, the sheath portion may be preferably made of somewhat high adsorbing material such as cotton so as to maximize its moisture adsorbing function, while other portions are made of a different material. Antifungal medications can be applied and/or permeated on the divider A to D for the same medical purpose.

Figure 3:
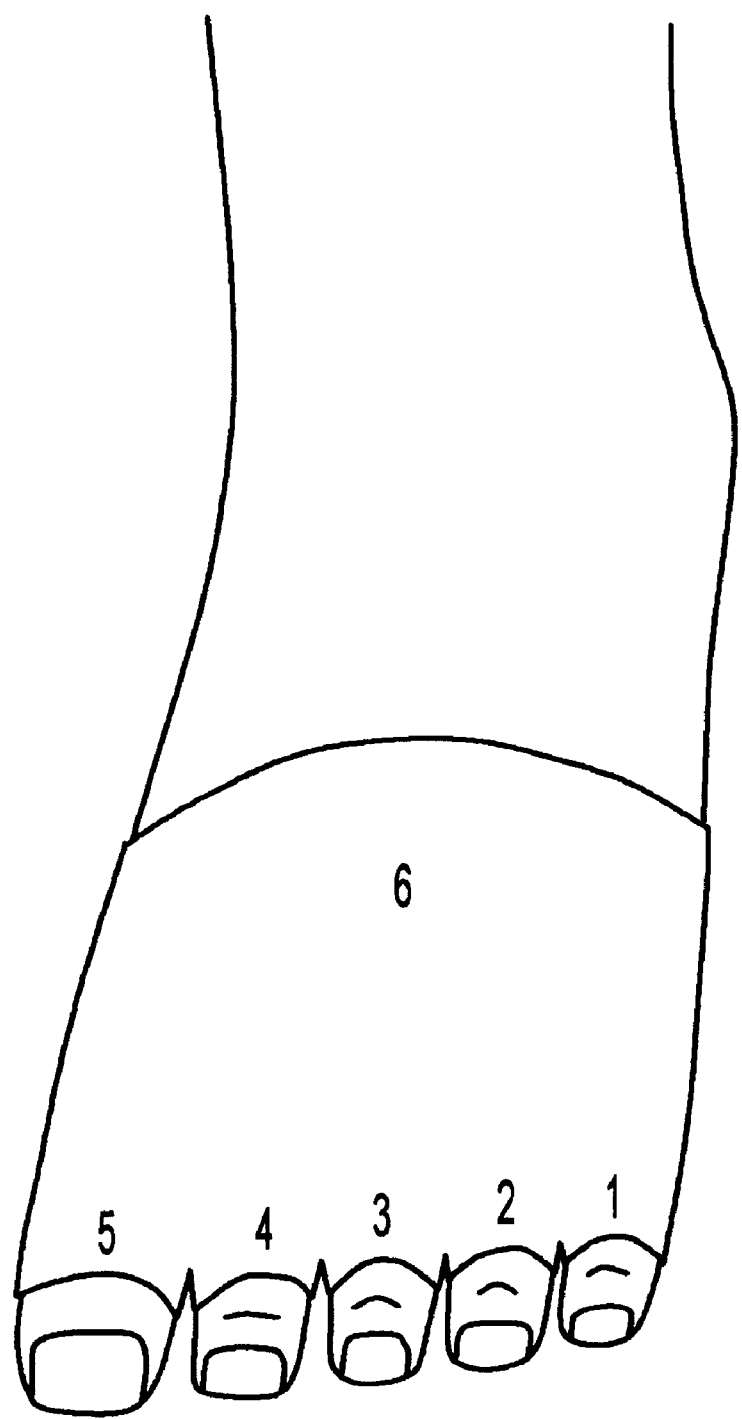
FIG. 3) is a perspective view of a sock including five sheaths when it is worn. In this embodiment the sheaths are open at the front. These sheaths reach and cover areas between toes while expose a tip portion of the wearer's toes. The five sheaths can be long and short, and can be in different size and shape. Every toe has its own open sheath when the sock is worn. Any sweat and secretion between toes is absorbed by the sheath reaching and covering the areas.

In FIG. 3 the sock includes five open sheaths numbered from 1 to 5 and a foot body portion 6. In this embodiment the sheaths are open at the front and a thin resilient circumferential band that encircles the foot body forms the body portion 6. The thin resilient circumferential band 6 is integral with, and extends from sheaths 1 to 5. The sheaths reach and cover areas between toes while expose a tip portion of a wearer's toes. The resilient circumferential band should prevent the sheath portion from skidding off the toes. These sheaths permit the wearer's toes to fit into each of them and allow the sock fabric to cover and fit into areas between every two adjacent toes, and are thus able to constantly absorb secretions from areas between toes. This keeps the skin in the area dry and therefore prevents microscopic fungi thriving between toes. The five sheaths can be long and short, and can be in different size and shape. Every toe has its own opening sheath when the sock is worn. Thus, sheath 5 is for the big toe, sheath 2 to 4 are for the three middle toes, and sheath 1 is for the little toe. Sheaths 1 to 5 are build along the root line of toes so as to correspond to the position of the five toes. Any sweat and secretion between toes is absorbed by the sock portion reaching and covering the area. The sock may be woven or knitted from many types of materials, such as natural materials cotton, wool and silk, or various types of manufactured fibers, including nylon, acrylic, polyester, polypropylene, and spandex, etc. The whole sock may be made of the same material, or alternatively, the sheath portion may be preferably made of somewhat high adsorbing material such as cotton so as to maximize its moisture adsorbing function while other portions are made of a different material. The sock can be worn alone or inside a regular sock. Antifungal medications can be applied and/or permeated on the sheaths for the same medical purpose.

As described above, the sock for preventing athlete's foot includes sheaths to reach and cover areas between toes, which are preferably made of a hygroscopic material on which a medicament can be applied and/or permeated. The number of sheaths can range from two to five. A sock of two sheaths may include a sheath for the little toe and a sheath for the four larger toes. It may also include a sheath for the big toe and a sheath for the four smaller toes. Other toe combinations for the sheath may also be adopted. Similarly a sock of three or four sheaths may have many sheath designs depending on the ways to combine toes for sheaths as well. A sock of five sheaths is preferable because all the foot skin between every two adjacent toes can be reached and covered by the sock. These sheaths should have appropriate shape so as to be fitted with human toes. It is best to manufacture different sized sock with different sized sheath in accordance with the size and shape of each person's feet and toes. The sheath portion may or may not be formed of the same fabric as the actual sock. The sheath portion may also be made elastic for engagement with larger and smaller toes. In addition, the sheath portion may be knitted thicker to absorb more efficiently the secretions between toes. The sock may have only a sheath/toe portion and a foot body portion (An example is shown in FIG.3). In this case a thin resilient circumferential band that encircles the foot body is integral with, and extends from the sheath portion. The resilient circumferential band should prevent the sheath portion from skidding off the toes. Preferably, besides the sheath portion, the sock may have a foot body portion, a heel portion and an ankle/calf portion so that the sock fits into the entire foot, ankle and/or leg.

While certain novel features of this invention have been shown and described and are pointed out in the annexed claims, it is not intended to be limited to the details described, since it will be understood that various modifications in the forms and details of the sock can be made by those skilled in the art without departing in any way from the essential characteristics of the generic or specific aspects of the present invention.

I claim:

1. A sock that comprises,
   a toe portion that is composed of five sheaths wherein the five sheaths are formed by four dividers inside the sock, said dividers are knitted to both a bottom and top part of the sock at the toe portion, and
   a foot body portion that covers the foot area between heel and toes;
   a heel portion that covers the heel, and
   an ankle portion that covers the ankle.

2. A sock that comprises,
   a toe portion wherein there is an inner layer of five sheaths, and
   a foot body portion that covers the foot area between heel and toes, and
   a heel portion that covers the heel, and
   an ankle portion that covers the ankle.

3. A sock that comprises,
   a toe portion that is composed of five sheaths wherein the five sheaths are independently knitted along root lines of the toes, and
   a foot body portion that covers the foot area between heel and toes, and
   a heel portion that covers the heel, and
   an ankle portion that covers the ankle.

* * * * *